United States Patent [19]

Kubo et al.

[11] Patent Number: 4,536,206

[45] Date of Patent: Aug. 20, 1985

[54] MITICIDAL COMPOSITION AND METHOD FOR CONTROLLING SPIDER MITES

[75] Inventors: Yoshiaki Kubo; Kaoru Takemura, both of Kagoshima; Shuichiro Kouno, Omiya, all of Japan

[73] Assignee: Wako Pure Chemical Industries, Ltd., Osaka, Japan

[21] Appl. No.: 541,841

[22] Filed: Oct. 14, 1983

[30] Foreign Application Priority Data

Oct. 15, 1982 [JP] Japan ................................ 57-180961

[51] Int. Cl.$^3$ ............................................. A01N 25/00
[52] U.S. Cl. ........................................... 71/3; 424/32; 106/15.05; 71/27
[58] Field of Search ............................................. 71/3

[56] References Cited

U.S. PATENT DOCUMENTS 4,048,369 9/1977 Johnson ............................... 428/262

*Primary Examiner*—William R. Dixon, Jr.
*Assistant Examiner*—Catherine A. Johnson
*Attorney, Agent, or Firm*—Armstrong, Nikaido, Marmelstein & Kubovcik

[57] ABSTRACT

A miticidal composition comprising a water-soluble acidic high polymer electrolyte of branching cross-linked polymer having a plurality of carboxyl groups as active ingredient and an aqueous medium is effective for various spider mites without causing chemical injury.

11 Claims, No Drawings

MITICIDAL COMPOSITION AND METHOD FOR CONTROLLING SPIDER MITES

BACKGROUND OF THE INVENTION

This invention relates to a miticidal composition and method for controlling spider mites. More particularly, this invention relates to a miticidal composition comprising a water-soluble acidic high molecular weight polymer of a branched crosslinked polymer obtained from one or more olefinic unsaturated carboxylic acids as active ingredient for various spider mites.

Among mites parasitizing plants, the most harmful ones are spider mites which harm fruit trees such as mandarin oranges, oranges, lemons, grapefruits, apples, etc., strawberries, eggplants, vegetables, tea plants, cucumbers and melons, etc., and woods. Further, since spider mites have a plurality of generations in one year and resistance to various synthetic miticides is found at an early stage commercially available miticides lose their practical control effects rapidly.

In order to solve such a problem there have been developed a solid paraffin emulsion and a emulsified machine oil, both exhibiting miticidal effective by physical action. But the former cannot prevent chemical injury, so that it is only used as spreader in small amounts. On the other hand, the latter is used mainly in the winter season when the metabolism of plants is lowered due to lower temperatures, in order to prevent chemical injury. It is also possible to purify a machine oil to give a spindle oil so as to lower the chemical injury. But it is well known that such an emulsified spindle oil cannot be used during the latter half of June to August, which period requires miticides most earnestly, in order to prevent the generation of oil stains, etiolation of leaves, latening of maturing of young fruits, degradation of quality of agricultural products such as fruits, caused by chemical injury. Particularly in the case of citrus fruits, since spraying of a machine oil emulsion before or after the spraying of N-(1,1,2,2-tetrachloroethylthio)-4-cyclohexene-1,2-dicarboximide (Difolatan), 2,3-dicyano-1,4-dithiaanthraquinone (Delan), or the like, which is a chemical for controlling scab disease, causes serious chemical injury such as leaf fall, the use of a machine oil emulsion is not allowable practically after the flowering period in an orchard sprayed with Difolatan, Delan, or the like.

SUMMARY OF THE INVENTION

It is an object of this invention to provide a miticidal composition overcoming the problems mentioned above.

This invention provides a miticidal composition comprising a water-soluble acidic high molecular weight branched and crosslinked polymer having a plurality of carboxyl groups as active ingredient and an aqueous medium as inert carrier.

DESCRIPTION OF PREFERRED EMBODIMENTS

The acidic high molecular weight polymer which is an active ingredient in the miticidal composition of this invention is a branched crosslinked polymer obtained from one or more olefinic unsaturated carboxylic acids preferably having 3 to 10 carbon atoms by crosslinking polymerization using a crosslinking agent.

Examples of the olefinic unsaturated carboxylic acids are acrylic acid, methacrylic acid, itaconic acid, chloroacrylic acid, cyanoacrylic acid, α-phenylacrylic acid, α-benzylacrylic acid, crotonic acid, maleic acid, fumaric acid, sorbic acid, etc. If necessary, one or more copolymerizable monomers can be used together. Examples of the copolymerizable monomers are acrylamide, methacrylamide, acrylonitrile, methacrylonitrile, lower alkyl esters of acrylic acid or methacrylic acid, such as methyl acrylate, ethyl acrylate, methyl methacrylate, ethyl methacrylate, etc., maleic anhydride, vinyl alkyl ethers such as vinyl methyl ether, vinyl ethyl ether, etc.

Examples of the crosslinking agent are divinylbenzene, divinyldioxane, sucrose polyallyl ether, alkylene glycol ethers such as diethylene glycol bisallyl ether, diethylene glycol bismethylallyl ether, dipropylene glycol bisallyl ether, dipropylene glycol bismethallyl ether, etc., pentaerythritol polyallyl ether, triallyl cyanurate, methylenebisacrylamide, alkylene bisacrylates, etc. The crosslinking agent is used in an amount of preferably 0.1 to 30% by weight, more preferably 0.5 to 10% by weight based on the total weight of monomer or monomers used.

The branched crosslinked polymer has a molecular weight of preferably 500,000 to 4,000,000, more preferably 1,000,000 to 3,000,000. The content of carboxyl groups in the branched crosslinked polymer is preferably 50 to 75%, more preferably 57 to 64% by weight.

These branched crosslinked polymers have been known as materials for adjusting shapes of pharmaceuticals, or as starting materials for cosmetics. It is a very surprising thing that these branched crosslinked polymers have miticidal action when used in special amounts. Further, these branched crosslinked polymers show no chemical injury and are sufficiently safe for men and beasts.

These branched crosslinked polymers are also available commercially, e.g., Carbopol available from B. F. Goodrich Chemical Co., Biscopal available from Takamatsu Ushi K.K., Junlon available from Nihon Junyaku Co., Ltd., HIVIS-Wako available from Wako Pure Chemical Industries, Ltd., etc.

As the aqueous medium, there can be used water alone or a mixture of water and one or more organic solvents miscible with water. Examples of the organic solvents miscible with water are alcohols, glycols, glycerol, dimethylformamide, dimethylsulfoxide, cyclic ethers such as dioxane, Cellosolves such as methyl Cellosolve, etc. These organic solvents are used in amounts not to harm plants and considering the safety in handling.

The miticidal composition of this invention can be prepared by uniformly mixing the acidic high molecular weight polymer with water or a mixture of water and one or more of the organic solvents mentioned above. If necessary, the miticidal composition may further contain one or more colorants, spreaders, and other additives which give other preferable effects of agricultural chemicals and/or enhance commodity values.

The content of the active ingredient in the miticidal composition is usually 3000 ppm or less, and preferably 100 to 2500 ppm (1 ppm=1/1,000,000). The content of higher than 3000 ppm can be used, but there is a tendency to increase a viscosity of the miticidal composition to a value too high to handle. Further, since a sufficient effect can be obtained at the concentration of 3000 ppm or less, the use of too much active ingredient is not necessary.

The miticidal composition of this invention can practically be used effectively any time at which spraying is necessary for any agricultural products which suffer from spider mites. Further, there cannot be observed any oil stains, which have been a serious disadvantage caused by using a purified machine oil emulsion or the like according to a conventional method, any inhibition of maturing of fruits, and any serious chemical injury caused by spraying before or after spraying of a germicide.

The miticidal composition of this invention is effective for spider mites such as apricot spider mite (*Eotetranychus boreus* Ehara), chestnut spider mite (*Eotetranychus pruni* Oudemans), sugarcane spider mite (*Oligonychus orthius* Rimando), citrus red mite (*Panonychus citri* McGregor), fruit tree red spider mite (*Panonychus ulmi* Koch), cryptomeria spider mite (*Oligonychus hondoensis* Ehara), spruce spider mite (*Oligonychus ununguis* Jacobi), etc. The miticidal composition of this invention is particularly effective for citrus red mite (*Panonychus citri* McGregor) and fruit tree red spider mite (*Panonychus ulmi* Koch).

As mentioned above, the miticidal composition of this invention is very useful in and greatly contributes to agriculture and horticulture.

This invention is illustrated in detail by way of the following Examples.

EXAMPLE 1

In a reactor equipped with a thermometer, a stirrer and a nitrogen introducing pipe, 11.8 parts by weight of acrylic acid, 108 parts by weight of benzene, 0.06 part by weight of azobisisobutyronitrile and 0.3 part by weight of diethylene glycol bisallyl ether were placed and reacted at 45°–50° C. for 12 hours in an atmosphere of nitrogen. The resulting crosslinked poly(acrylic acid) had a molecular weight of 2,500,000 to 3,000,000 and a carboxylic group content of 60.5% by weight.

To 97 parts by weight of water, 3 parts by weight of the crosslinked poly(acrylic acid) as the acidic high molecular weight was mixed uniformly with stirring. The resulting mixture was diluted with water as shown in Table 1 to give five compositions having different concentrations of the active ingredient. Miticidal action was tested as follows.

In a laboratory dish having a diameter of 9 cm, 30 ml agar solution was placed. Immediately before the solidification of agar solution, a citrus leaf having a prescribed area was placed on the agar solution and adhered thereto. Then, 25 female adults of citrus red mite (*Panonychus citri* McGregor) were inoculated per laboratory dish. The test was repeated twice by using two laboratory dishes per one kind of composition. A miticidal composition of this invention having a concentration as listed in Table 1 was sprayed on a laboratory dish placed on a turn table for 10 seconds, respectively, and life or death of citrus red mites after 24 hours was observed. The results are shown in Table 1.

COMPARATIVE EXAMPLE 1

Water-diluted solutions as listed in Table 1 were prepared by mixing water with a purified machine oil emulsion (Spindlon emulsion=97 parts by weight of spindle oil+3 parts by weights of emulsifier). The miticidal activity was tested in the same manner as described in Example 1. The results are shown in Table 1.

TABLE 1

| | Concentration of active ingredient (ppm) | Death rate (%) | $LC_{50}$, $LC_{90}$ values |
|---|---|---|---|
| Composition of Example 1 | 1000 | 100 | $LC_{50}$ = 110 ppm |
| | 500 | 92 | $LC_{90}$ = 410 ppm |
| | 250 | 76 | |
| | 125 | 66 | |
| | 63 | 8 | |
| Composition of Comparative Example 1 | 2000 | 78 | $LC_{50}$ = 800 ppm |
| | 1000 | 56 | $LC_{90}$ = 4150 ppm |
| | 500 | 34 | |
| | 250 | 18 | |
| | 125 | 6 | |

In Table 1, $LC_{50}$ and $LC_{90}$ values mean the concentrations causing death rate of 50% and 90%, respectively. As is clear from Table 1, the miticidal composition of this invention can give the same miticidal effect ($LC_{90}$) as that of Comparative Example 1 in the concentration of about 1/10 of the concentration of Comparative Example 1.

EXAMPLE 2

When an acidic high molecular weight branched and crosslinked copolymer of acrylic acid and maleic anhydride crosslinked by using sucrose polyallyl ether (produced according to a process disclosed in Japanese Patent Application Kokoku (Post-Exam Publn) No. 4141/57) was used in place of the acidic high molecular weight polymer of Example 1, the same results as obtained in Example 1 were obtained.

Further, when Carbopol available from B. F. Goodrich Chemical Co., was used in place of the acidic high polymer of Example 1, the same results as obtained in Example 1 were obtained.

EXAMPLE 3

To a mixture of 73 parts by weight of water and 24 parts by weight of glycerol, 3 parts by weight of the same acidic high polymer as used in Example 1 was mixed uniformly with stirring. The resulting mixture was diluted with water as shown in Table 2 to give two compositions having different concentrations of the active ingredient. Miticidal action was tested as follows.

In a laboratory dish having a diameter of 9 cm, 30 ml of agar solution was placed. Immediately before the solidification of agar solution, an apple leaf having a prescribed area was placed on the agar solution and adhered thereto. Then, 25 female adults of fruit tree red spider mite (*Panonychus ulmi* Koch) were inoculated per laboratory dish. The test was repeated twice by using two laboratory dishes per one kind of composition. A miticidal composition of this invention having a concentration as listed in Table 2 was sprayed on a laboratory dish placed on a turn table for 10 seconds, respectively, and life or death of fruit tree red spider mites after 24 hours was observed. The results are shown in Table 2.

For comparison, the composition of Comparative Example 1 having concentrations as listed in Table 2 was subjected to the same miticidal test as mentioned above. The results are also shown in Table 2.

TABLE 2

| | Concentration of active ingredient (ppm) | Death rate (%) |
|---|---|---|
| Composition | 1250 | 96 |

TABLE 2-continued

| | Concentration of active ingredient (ppm) | Death rate (%) |
|---|---|---|
| of Example 3 | 625 | 94 |
| Composition of Comparative Example 1 | 5000 | 90 |
| | 2500 | 78 |
| No treatment | — | 0 |

As is clear from Table 2, the miticidal composition of this invention can give the same miticidal effect in a concentration of about ¼ as that of Comparative Example 1.

EXAMPLE 4

When an acidic high molecular weight branched and crosslinked copolymer of methacrylic acid crosslinked by using 3% tetraallyloxyethane (produced according to a process disclosed in U.S. Pat. No. 3,817,949) was used in place of the acidic high molecular weight polymer of Example 3, the same results as obtained in Example 3 were obtained.

Further, when Carbopol available from B. F. Goodrich Chemical Co., was used in place of the acidic high molecular weight polymer of Example 3, the same results as obtained in Example 3 were obtained.

EXAMPLE 5

The miticidal composition of Example 1 was diluted with water as shown in Table 3. Each composition was sprayed by using a small sprayer over 3-years old citrus unshiu (Okitsu, Japan) in a pot, a 2-years old sweet orange (Amanatsu, a commercial name) in a pot, a 3-years old orange (*citrus sinensis*) in a pot, and a 3-years old grapefruit (*citrus paradisi*) in a pot to evaluate control effect against citrus red mite. On testing, 30 citrus leaves per pot were marked and the number of adult of citrus red mite parasitizing on the leaves was counted with the lapse of time using five pots per kind of miticidal composition.

The control effect was calculated as follows:

$$\text{Control effect} = \left(1 - \frac{Cb \sum_{i=1}^{n} Ta_i}{Tb \sum_{i=1}^{n} Ca_i}\right) \times 100\%$$

wherein
Cb: the number of mites before the treatment in non-treating region
Tb: the number of mites before the treatment in treating region
Ca$_i$: the accumulated number of mites 4, 7, 14, 21 and 30 days after the treatment in non-treating region
Ta$_i$: the accumulated number of mites 4, 7, 14, 21 and 30 days after the treatment in treating region.

For comparison, the composition of Comparative Example 1 having a concentration as listed in Table 3 was subjected to the same miticidal test as mentioned above. The results are also shown in Table 3.

TABLE 3

| | Concentration of active ingredient (ppm) | Control effect (%) | | | |
|---|---|---|---|---|---|
| | | Citrus unshiu | Sweet orange | Orange (Citrus sinensis) | Grapefruit (Citrus paradisi) |
| Composition of this invention | 2500 | 91.0 | 94.1 | 92.5 | 93.8 |
| | 1250 | 73.9 | 93.5 | 90.3 | 93.3 |
| Composition of Comparative Example 1 | 5000 | 90.0 | 93.2 | 88.9 | 92.8 |
| No treatment | — | 0 | 0 | 0 | 0 |

As is clear from Table 3, the miticidal composition of this invention is very excellent.

When the same acidic high same molecular weight polymer as used in Example 2 was used, the same excellent effect as shown in Table 3 was obtained.

EXAMPLE 6

(Chemical injury)

Oil stains appearing on the citrus leaves as result of chemical injury were observed with the lapse of time when the test of Example 5 for measuring the effects of compositions was conducted. The results are shown in Table 4.

TABLE 4

| | | Composition of this invention | | Composition of Comparative Example 1 | | No treatment |
|---|---|---|---|---|---|---|
| Concentration of active ingredient (ppm) | | 2500 | 1250 | 5000 | 2500 | — |
| | Days after | | | | | |
| Citrus unshiu | 7 | — | — | ++ | ++ | — |
| | 14 | — | — | ++ | ++ | — |
| | 21 | — | — | +++ | ++ | — |
| | 30 | — | — | +++ | +++ | — |
| Sweet orange (Amanatsu) | 7 | — | — | + | + | — |
| | 14 | — | — | + | + | — |
| | 21 | — | — | + | ++ | — |
| | 30 | — | — | + | ++ | — |
| Orange (*citrus cinensis*) | 7 | — | — | + | + | — |
| | 14 | — | — | ++ | + | — |
| | 21 | — | — | ++ | + | — |
| | 30 | — | — | ++ | ++ | — |
| Grapefruit (*citrus paradisi*) | 7 | — | — | + | + | — |
| | 14 | — | — | + | + | — |
| | 21 | — | — | + | + | — |
| | 30 | — | — | ++ | + | — |

Note
—: No change was observed on the leaves.
+: Oil stains appreared on 1 to 33% of the rear leaf area.
++: Oil stains appeared on 34 to 66% of the rear leaf area.
+++: Oil stains appeared on 67 to 100% of the rear leaf area.

As is clear from Table 4, the miticidal composition of this invention is by far safer for plants compared with the conventional purified machine oil emulsion.

EXAMPLE 7

(Chemical injury)

Chemical injury of the miticidal composition of this invention caused to citrus (*citrus unshiu*) leaves was tested by spraying the composition of Example 1 having concentrations as listed in Table 5 before or after the spraying of Difolatan (hydrated form), which is an agent for controlling scab disease that is a serious disease for citrus fruits, having concentrations as listed in Table 5. That is, the rates of falling of citrus leaves in the case of spraying the miticidal composition of this invention, followed by spraying Difolatan after 2 weeks later, or in the case of spraying Difolatan, followed by spraying of the miticidal composition of this invention, were obtained. The results are shown in Table 5.

For comparison, the rates of falling of citrus leaves were also tested in the case of spraying a spindle oil emulsion, followed by spraying Difolatan after 2 weeks later, and vice versa. The results are shown in Table 5.

As is clear from Table 5, the chemical injury of the miticidal composition of this invention is very slight compared with the conventional miticidal composition.

TABLE 5

| | First spraying | | Spraying after 2 weeks | | | |
|---|---|---|---|---|---|---|
| Run No. | Treating agent | Concentration of active ingredient (ppm) | Treating agent | Concentration of active ingredient (ppm) | Number of leaves tested | Leaf falling rate (%) |
| 1 | Miticidal composition of this invention | 2500 | Difolatan (hydrated form) | 800 | 200 | 3.5 |
| 2 | | 1250 | | 800 | 200 | 6.5 |
| 3 | Difolatan (hydrated form) | 800 | Miticidal composition of this invention | 2500 | 200 | 3.0 |
| 4 | | 800 | | 1250 | 200 | 4.0 |
| 5 | Spindle oil emulsion | 10000 | Difolatan (hydrated form) | 800 | 200 | 43.0 |
| 6 | Difolatan (hydrated form) | 800 | Spindle oil emulsion | 10000 | 200 | 47.5 |
| 7 | No treatment | | | | 200 | 2.5 |

EXAMPLE 8

(Chemical injury)

The process of Example 7 was repeated except for using orange (*citrus sinensis*) leaves in place of citrus leaves. The same results as obtained in Example 7 were obtained.

What is claimed is:

1. A miticidal composition consisting essentially of a water-soluble acidic high molecular weight branched and crosslinked polymer having a plurality of carboxyl groups as active ingredient and an aqueous medium as inert carrier, wherein the concentration of the active ingredient is at most 3000 ppm.

2. A composition according to claim 1, wherein the content of carboxyl groups in the branched crosslinked polymer is 50 to 75% by weight.

3. A composition according to claim 1, wherein the concentration of the active ingredient in the composition is 3000 to 100 ppm.

4. A composition according to claim 1, wherein the aqueous medium is water.

5. A composition according to claim 1, wherein the aqueous medium is a mixture of water and one or more organic solvents miscible with water.

6. A composition according to claim 1, wherein the branched crosslinked polymer has a molecular weight of 500,000 to 4,000,000.

7. A composition according to claim 6, wherein the branched crosslinked polymer is obtained from at least one olefinic unsaturated carboxylic acid selected from the group consisting of acrylic acid, methacrylic acid, maleic acid, fumaric acid, itaconic acid, chloroacrylic acid, cyanoacrylic acid, α-phenylacrylic acid, α-benzylacrylic acid, crotonic acid, and sorbic acid.

8. A composition according to claim 6, wherein the branched crosslinked polymer is a copolymer of at least one olefinic unsaturated carboxylic acid selected from the group consisting of acrylic acid, methacrylic acid, itaconic acid, chloroacrylic acid, cyanoacrylic acid, α-phenylacrylic acid, α-benzylacrylic acid, crotonic acid, sorbic acid, maleic acid and fumaric acid, and at least one copolymerizable monomer selected from the group consisting of acrylamide, methacrylamide, acrylonitrile, methacrylonitrile, methyl acrylate, ethyl acrylate, methyl methacrylate, ethyl methacrylate, maleic anhydride, vinyl methyl ether and vinyl ethyl ether.

9. A composition according to claim 6, wherein the branched crosslinked polymer is obtained by using a crosslinking agent in an amount of 0.1 to 30% by weight based on the total weight of monomer or monomers used.

10. A composition according to claim 9, wherein the crosslinking agent is at least one member selected from the group consisting of divinylbenzene, divinyldioxane, sucrose polyallyl ether, diethylene glycol bisallyl ether, diethylene glycol bismethallyl ether, dipropylene glycol bisallyl ether, dipropylene glycol bismethallyl ether, pentaerythritol polyallyl ether, triallyl cyanurate, methylenebisacrylamide, and an alkylene bisacrylate.

11. A method for controlling spider mites comprising applying to mites in their natural habitats a miticidally effective amount of a composition consisting essentially of a water-soluble branched crosslinked polymer having a plurality of carboxyl groups and a molecular weight of 500,000–4,000,000, and an aqueous carrier, wherein the concentration of the active ingredient is at most 3000 ppm.

* * * * *